United States Patent [19]

Wilshire et al.

[11] 4,420,614
[45] Dec. 13, 1983

[54] CYANOPHENOXYBENZYL AMINES

[75] Inventors: Colin Wilshire, Doncaster East; Rene Jongen, Parkville, both of Australia

[73] Assignee: ICI Australia Limited, Victoria, Australia

[21] Appl. No.: 300,191

[22] Filed: Sep. 8, 1981

[30] Foreign Application Priority Data

Oct. 3, 1980 [AU] Australia .............................. PE5871

[51] Int. Cl.³ .................. C07D 295/14; C07D 207/16; C07C 121/78
[52] U.S. Cl. .................... 544/163; 544/224; 544/335; 544/336; 544/398; 546/230; 546/330; 548/341; 548/561; 548/565; 548/569; 260/465 D; 260/465 E
[58] Field of Search .................. 260/465 E; 544/163, 544/224, 335, 336, 398; 546/230, 330; 548/341, 561, 565, 569

[56] References Cited

U.S. PATENT DOCUMENTS 4,110,362  8/1978  Sheldon et al. ................ 260/465 D
4,167,576  9/1979  Miller et al. ................. 260/465 E X

FOREIGN PATENT DOCUMENTS 2053219  2/1981  United Kingdom .

OTHER PUBLICATIONS

Kuraray Co. Ltd., Chemical Abstracts, vol. 94, 65342y (1981).

*Primary Examiner*—Dolph H. Torrence
*Attorney, Agent, or Firm*—Cushman, Darby & Cushman

[57] ABSTRACT

The invention concerns novel compounds of the formula I

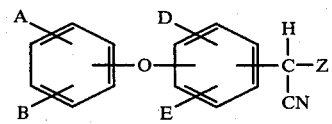

wherein A, B, D and E are chosen from hydrogen, halogen, $C_1$ to $C_6$ alkyl, $C_1$ to $C_6$ haloalkyl and $C_1$ to $C_6$ alkoxy and Z is a tertiary or quaternary amino group.

The compounds are useful intermediates for the preparation of pyrethroids. In further embodiments the invention provides processes for the preparation of the compounds of formula I and processes for the synthesis of pyrethroids utilizing the compounds of formula I.

6 Claims, No Drawings

CYANOPHENOXYBENZYL AMINES

This invention relates to α-cyanophenoxybenzylamine derivatives, to processes for the preparation of such derivatives and their use as intermediates in the preparation of pyrethroids.

It has now been found that certain α-cyanophenoxybenzylamine derivatives are useful synthetic intermediates for the preparation of pyrethroids which contain an α-cyano substituent in the alcohol moiety of the carboxylic acid ester.

Accordingly the invention provides a compound of formula I

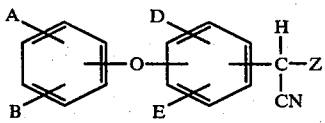

wherein:
A, B, D and E are independently chosen from the group consisting of hydrogen, halogen, $C_1$ to $C_6$ alkyl, $C_1$ to $C_6$ haloalkyl and $C_1$ to $C_6$ alkoxy; and Z is chosen from $NR^1R^2$ and $N^{\oplus}R^1R^2R^3 X^{\ominus}$ wherein:

$R^1$ and $R^2$ are independently chosen from the group consisting of $C_1$ to $C_6$ alkyl, phenyl benzyl, and the groups phenyl and benzyl wherein in each group the phenyl ring is substituted with from one to three substituents chosen from the group consisting of halogen, nitro, cyano, hydroxy, $C_1$ to $C_6$ alkyl, $C_1$ to $C_6$ alkoxy and $C_1$ to $C_6$ haloalkyl, or $R^1$ and $R^2$ are linked to form a three to seven membered heterocyclic ring;

$R^3$ is chosen from the group consisting of $C_1$ to $C_6$ alkyl, phenyl, benzyl, and the groups phenyl and benzyl wherein in each group the phenyl ring is substituted with from one to three substituents chosen from the group consisting of halogen, nitro, cyano, hydroxy, $C_1$ to $C_6$ alkyl, $C_1$ to $C_6$ alkoxy and $C_1$ to $C_6$ haloalkyl, or $N^{\oplus}R^1R^2R^3$ is a pyridinium, pyrazinium, pyrimidinium or pyridazinium ring; and $X^{\ominus}$ is the anion of an organic or an inorganic acid.

The compounds of formula I have a chiral centre and therefore the racemic compounds may be resolved into their enantiomers. Therefore, the present invention includes the individual stereo isomers of the compounds and mixtures of those stereo isomers in addition to the racemic mixture of stereo isomers.

Examples of suitable A, B, D and E include hydrogen, halogen, methyl, trifluoromethyl and methoxy.

Examples of suitable Z, wherein Z is the group $NR^1R^2$, include N,N-dimethylamino, N,N-diethylamino, N,N-di(n-propyl)amino, N-isobutyl-N-methylamino, N-methyl-N-benzylamino, 1-pyrrolyl, 1-imidazolyl, 1-pyrrolidinyl, 1-pyrrolinyl, 1-imidazolinyl, piperidino, 1-piperazinyl and morpholino.

Examples of suitable Z, wherein Z is the group $N^{\oplus}R^1R^2R^3 X^{\ominus}$, include trimethylammonio, triethylammonio, N,N-diethyl-N-methylammonio, N-methyl-N,N-di-(n-propyl)ammonio, N-isobutyl-N,N-dimethylammonio, N-benzyl-N,N-dimethylammonio, 1-methyl-1-pyrrolio, 1-methyl-1-imidazolio, 1-methyl-1-pyrrolidinio, 1-methyl-1-pyrrolinio, 1-methyl-1-imidazolinio, 1-methyl-1-piperidinio, 4-methyl-4-morpholinio, 1-pyridinio, 1-pyrazinio, 1-pyrimidinio and 1-pyridazinio.

Examples of suitable $X^{\ominus}$ include the anions of strong acids, such as, hydrochloric acid, hydrobromic acid, hydriodic acid, sulfuric acid, nitric acid, methyl hydrogen sulfate, ethyl hydrogen sulfate, tetrafluoroboric acid, hexa fluorophosphoric acid, hexafluoroantimonoic acid, methansulfonic acid, fluorosulfonic acid, fluoromethanesulfonic acid and trifluoromethanesulfonic acid.

Preferred A, B, D and E include hydrogen and halogen.

Preferred Z is chosen from the groups $NR^1R^2$ and $N^{\oplus}R^1R^2R^3 X^{\ominus}$ wherein:

$R^1$ and $R^2$ are independently chosen from the group consisting of $C_1$ to $C_4$ alkyl, phenyl and benzyl or $R^1$ and $R^2$ are linked to form a heterocyclic ring chosen from the group consisting of 1-pyrrolyl, 1-imidazolyl, 1-pyrrolidinyl, 1-pyrrolinyl, 1-imidazolinyl, piperidino, 1-piperazinyl and morpholino;

$R^3$ is chosen from the group consisting of $C_1$ to $C_4$ alkyl, phenyl and benzyl or $N^{\oplus}R^1R^2R^3$ is a pyridinium, pyrazinium, pyrimidinium or pyridazinium ring; and $X^{\ominus}$ is the anion of a strong acid.

More preferred Z is chosen from the groups $NR^1R^2$ and $N^{\oplus}R^1R^2R^3 X^{\ominus}$ wherein:

$R^1$ and $R^2$ are independently chosen from $C_1$ to $C_4$ alkyl or $R^1$ and $R^2$ are linked to form a heterocyclic ring chosen from the group consisting of 1-pyrrolyl, 1-pyrrolidinyl, piperidino and morpholino;

$R^3$ is chosen from $C_1$ to $C_4$ alkyl; and $X^{\ominus}$ is the anion of a strong acid.

Specific examples of compounds of the invention include:

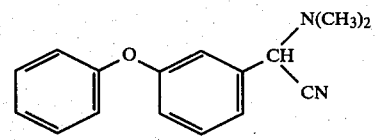

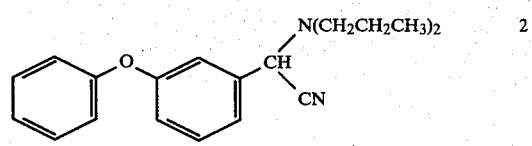

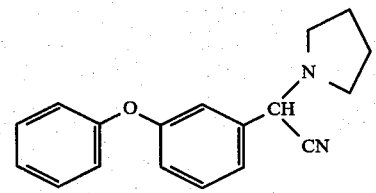

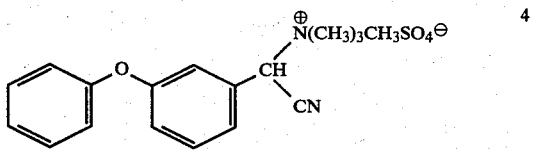

-continued

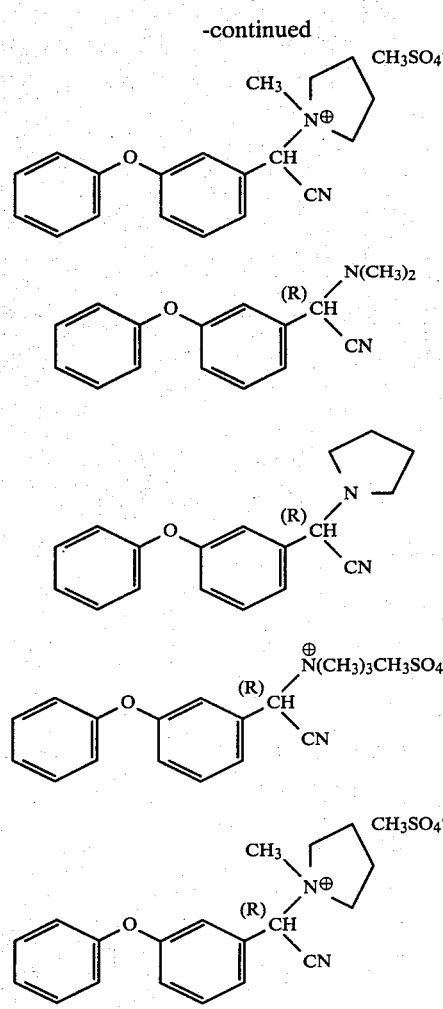

Preferred compounds of formula I are those compounds in which the phenyl ring of the benzyl group is substituted in the 3-position by the phenoxy group, that is, compounds of formula II:

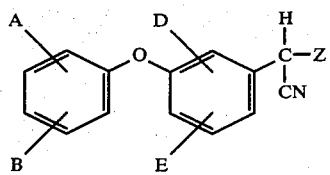

The compounds of the invention may be prepared, for example, by the amination of an α-cyanophenoxybenzyl derivative or the cyanoamination of a phenoxybenzaldehyde derivative and in further embodiments the invention provides processes for the preparation of the compounds of formula I.

Compounds of formula I wherein Z is the group $NR^1R^2$ wherein $R^1$ and $R^2$ are as hereinbefore defined, that is compounds of formula Ia, may be prepared by reacting an α-cyanophenoxybenzyl derivative of formula IV, wherein L is a leaving group (for example, alkylsulfonyl, arylsulfonyl, chlorine, bromine or iodine), with an amine of formula V, wherein $R^{26}$ is hydrogen or $R^1$ as hereinbefore defined and $R^{27}$ is hydrogen or $R^2$ as hereinbefore defined, and if $R^{26}$ and/or $R^{27}$ is hydrogen, alkylating as required to give a compound of formula Ia according to SCHEME A.

SCHEME A

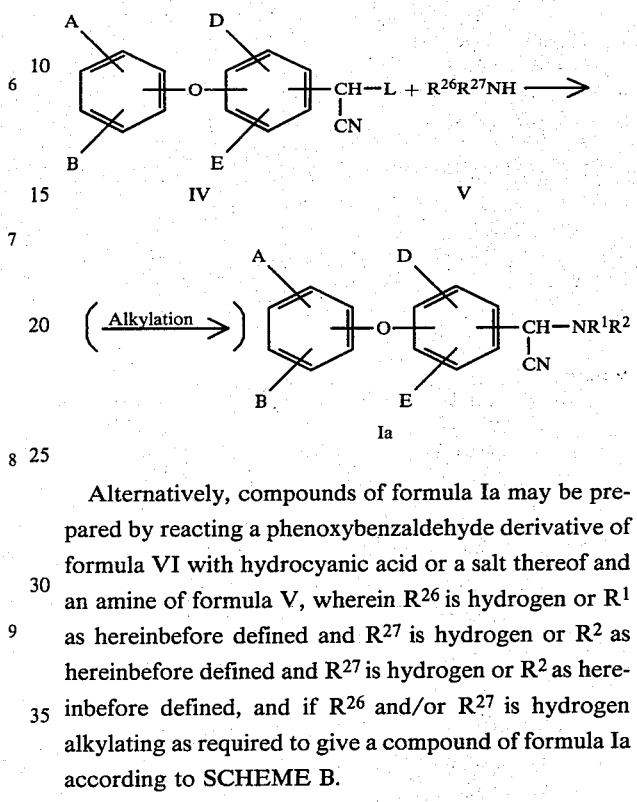

Alternatively, compounds of formula Ia may be prepared by reacting a phenoxybenzaldehyde derivative of formula VI with hydrocyanic acid or a salt thereof and an amine of formula V, wherein $R^{26}$ is hydrogen or $R^1$ as hereinbefore defined and $R^{27}$ is hydrogen or $R^2$ as hereinbefore defined and $R^{27}$ is hydrogen or $R^2$ as hereinbefore defined, and if $R^{26}$ and/or $R^{27}$ is hydrogen alkylating as required to give a compound of formula Ia according to SCHEME B.

SCHEME B

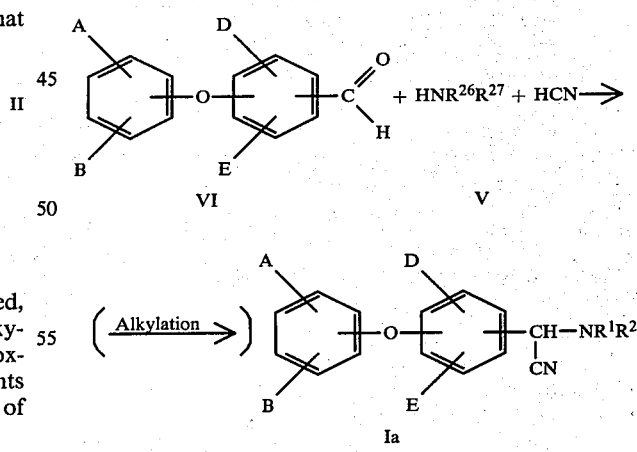

Compounds of formula I wherein Z is the group $N^{\oplus}R^1R^2R^3X^{\ominus}$ wherein $R^1$, $R^2$, $R^3$ and $X^{\ominus}$ are as hereinbefore defined, that is compounds of formula Ib, may be prepared by reacting a compound of formula Ia with an alkylating agent of formula VII according to SCHEME C.

SCHEME C

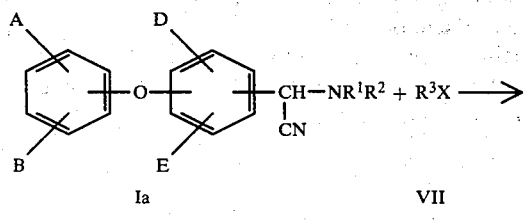

Alternatively, compounds of formula Ib may be prepared directly by the reaction of a compound of formula IV, wherein A, B, D, E and L are as hereinbefore defined, with a tertiary amine of formula VIII, wherein R¹, R², R³ and X⊖ are as hereinbefore defined, according to Scheme D (the leaving group L is displaced to form the anion X⊖).

SCHEME D

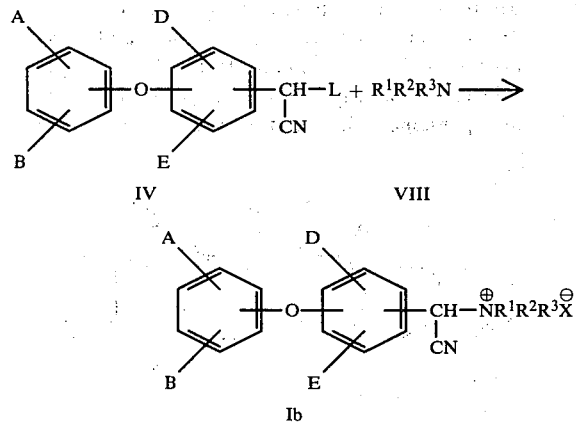

The reactions illustrated in Schemes A, B, C and D above are preferably carried out in the presence of a solvent. Suitable solvents include ketones such as, for example, methyl ethyl ketone, acetone, and methyl isobutyl ketone, alcohols such as, for example, methanol, ethanol, n-propanol and isopropanol, and dipolar aprotic solvents such as, for example, dimethylformamide, dimethylacetamide, dimethylsulfoxide, N-methylpyrrolidone, hexamethylphosphoramide and sulfolan.

The conditions required to effect the reactions illustrated in Schemes A, B, C and D and outlined above will vary according to the nature of the reactants and the solvent used. The reactions may be carried out at ambient temperature, however, if required, heat may be applied. Usually a reaction temperature in the range of from 15° to 150° C. and a reaction time of between 0.5 and 20 hours is satisfactory. However, higher or lower reaction temperatures, and/or shorter or longer reaction times may be employed if desired.

The compounds of the invention are useful intermediates for the preparation of a range of low-toxicity, pyrethroid pesticides of the formula X

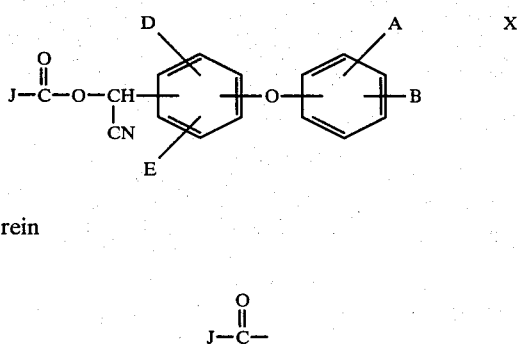

wherein $$J-\overset{O}{\underset{\|}{C}}-$$

is a pyrethrin acid moiety or a pyrethroid acid moiety. Suitable J include groups of the formulae:

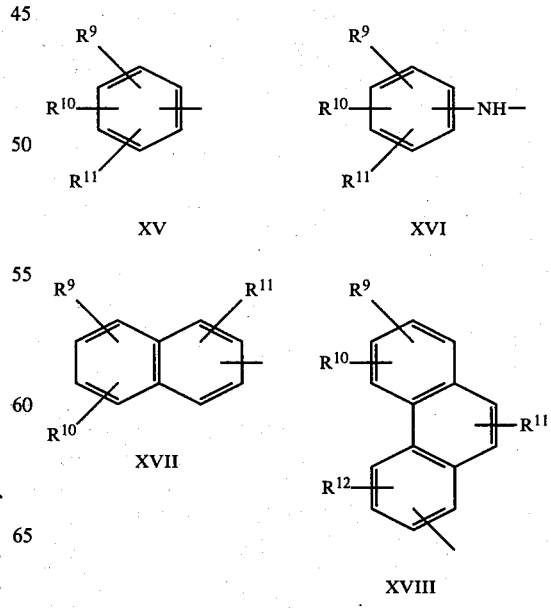

wherein V represents a substituted aromatic group or an unsaturated alicyclic group or an alkenyl group and is selected from the group consisting of the formulae -continued

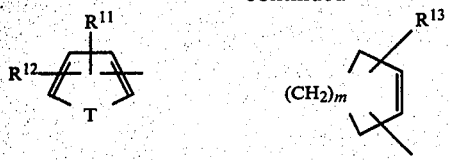

XIX XX

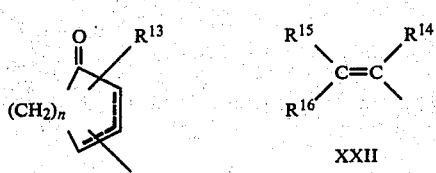

XXI

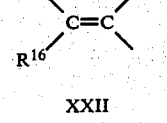

XXII in which
R$^9$ and R$^{10}$ are independently chosen from hydrogen, halogen, cyano, nitro, C$_1$ to C$_6$ alkyl optionally substituted with halogen atoms or C$_1$ to C$_6$ alkoxy, C$_2$ to C$_6$ alkenyl optionally substituted with halogen atoms, C$_2$ to C$_6$ alkynyl optionally substituted with halogen atoms, C$_1$ to C$_6$ alkoxy optionally substituted with halogen atoms, C$_1$ to C$_6$ alkylthio, C$_1$ to C$_6$ alkylsulfinyl, acyl, acyloxy, C$_1$ to C$_6$-(alkoxy)carbonyl, C$_2$ to C$_6$-(alkenyloxy)carbonyl and C$_2$ to C$_6$-(alkynyloxy)carbonyl, or R$^9$ and R$^{10}$ may jointly form a methylene dioxy, tetramethylene or trimethylene group; R$^{11}$ and R$^{12}$ are independently chosen from hydrogen, halogen, cyano, nitro, C$_1$ to C$_6$ alkyl optionally substituted with halogen atoms or C$_1$ to C$_6$ alkoxy, C$_2$ to C$_6$ alkenyl optionally substituted with halogen atoms, C$_2$ to C$_6$ alkynyl optionally substituted with halogen atoms, C$_1$ to C$_6$ alkoxy, C$_1$ to C$_6$ alkylthio, C$_1$ to C$_6$ alkylsulfinyl, acyl, acyloxy, C$_1$ to C$_6$-(alkoxy)carbonyl, C$_2$ to C$_6$-(alkeyloxy)carbonyl and C$_2$ to C$_6$-(alkynyloxy)carbonyl; T represents an oxygen atom or a sulfur atom;
R$^{13}$ is chosen from hydrogen, halogen, cyano, nitro and C$_1$ to C$_6$ alkyl; m and n are independently integers of from 1 to 3; the dotted line in formula XX represents a double bond present at a position either conjugated with or non-conjugated with the ketone group (C=O); R$^{14}$, R$^{15}$ and R$^{16}$ are independently chosen from hydrogen, C$_1$ to C$_6$ alkyl, C$_2$ to C$_6$ alkenyl, C$_2$ to C$_6$ alkynyl, halogen, acyl and acyloxy;
W represents a straight or branched chain C$_1$ to C$_6$ alkyl group optionally substituted with halogen, a straight or branched chain C$_2$ to C$_6$ alkenyl group optionally substituted with halogen, a straight or branched chain C$_2$ to C$_6$ alkynyl group, C$_1$ to C$_6$ alkoxy, cyano or a C$_3$ to C$_7$ alicyclic group;
G is hydrogen or fluorine;
Y is the group R$^{18}$R$^{19}$C=CR$^{17}$ in which R$^{17}$ is hydrogen or C$_1$ to C$_6$ alkyl; R$^{18}$ is hydrogen, halogen or C$_1$ to C$_6$ alkyl optionally substituted with halogen atoms; R$^{19}$ is chosen from the group consisting of hydrogen, halogen, C$_1$ to C$_6$ alkyl optionally substituted with halogen atoms, C$_1$ to C$_6$ alkyl substituted with C$_1$ to C$_6$ alkoxy, C$_1$ to C$_6$ alkyl substituted with C$_2$ to C$_6$ alkenyloxy, C$_1$ to C$_6$ alkyl substituted with C$_2$ to C$_6$ alkynyloxy, C$_1$ to C$_6$-(alkoxy)carbo- nyl, acyl, a substituent of the formula R$^{21}$R$^{22}$C=CR$^{20}$— wherein R$^{20}$, R$^{21}$ and R$^{22}$ are individually hydrogen or C$_1$ to C$_6$ alkyl, and a substituent of the formula R$^{23}$ON=CH— wherein R$^{23}$ is hydrogen or C$_1$ to C$_6$ alkyl or C$_2$ to C$_6$ alkenyl or C$_2$ to C$_6$ alkynyl; or R$^{18}$ and R$^{19}$ jointly may form a cycle of formula

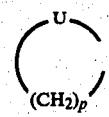

XXII wherein U is

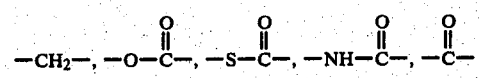

and p is an integer of from 2 to 5;
R$^6$ is hydrogen or C$_1$ to C$_6$ alkyl;
R$^4$ and R$^5$ are independently chosen from hydrogen, halogen and C$_1$ to C$_6$ alkyl, or R$^4$ and R$^5$ jointly form an ethylene, trimethylene, tetramethylene or pentamethylene bridging group;
R$^7$ and R$^8$ are independently chosen from hydrogen, C$_1$ to C$_6$ alkyl, C$_1$ to C$_6$ haloalkyl, halogen and phenyl optionally substituted with one or more groups or atoms chosen from halogen, nitro, cyano, C$_1$ to C$_6$ alkyl, C$_1$ to C$_6$ haloalkyl and C$_1$ to C$_6$ alkoxy or R$^7$ and R$^8$ jointly form a bridging group selected from ethylene, trimethylene, tetramethylene, pentamethylene and groups of the formulae

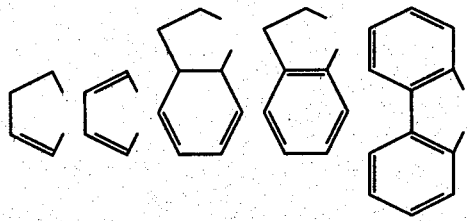

XXIV  XXV  XXVI  XXVII  XXVIII

Q is selected from C$_1$ to C$_6$ alkyl, C$_2$ to C$_6$ alkenyl, C$_2$ to C$_6$ alkynyl and the group

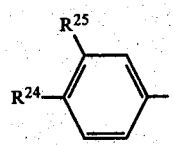

XXIX in which R$^{24}$ is chosen from hydrogen, C$_1$ to C$_3$ alkoxy, C$_1$ to C$_3$ alkylthio, C$_1$ to C$_2$ alkyl, nitro, fluoro, chloro, bromo and amino; R$^{25}$ is chosen from hydrogen and methyl; or R$^{24}$ and R$^{25}$ jointly is a methylenedioxy bridging group.

Accordingly, in yet a further aspect the invention provides a process for the preparation of a compound of formula X

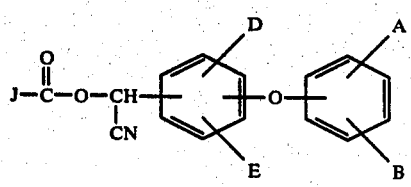

which process comprises reacting a carboxylic acid derivative of formula IX, or a salt thereof,

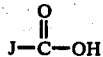

with a compound of formula Ib

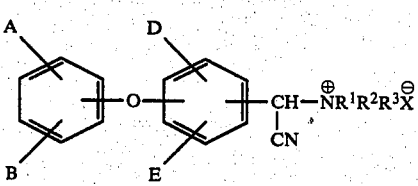

and wherein A, B, D, E, J, $R^1$, $R^2$, $R^3$ and $X^\ominus$ are as hereinbefore defined.

Suitable salts of the carboxylic acid derivative of formula IX include, for example, alkali metal and alkaline earth metal salts.

Examples of specific groups of formula J include those groups illustrated in Table 1 below:

TABLE 1

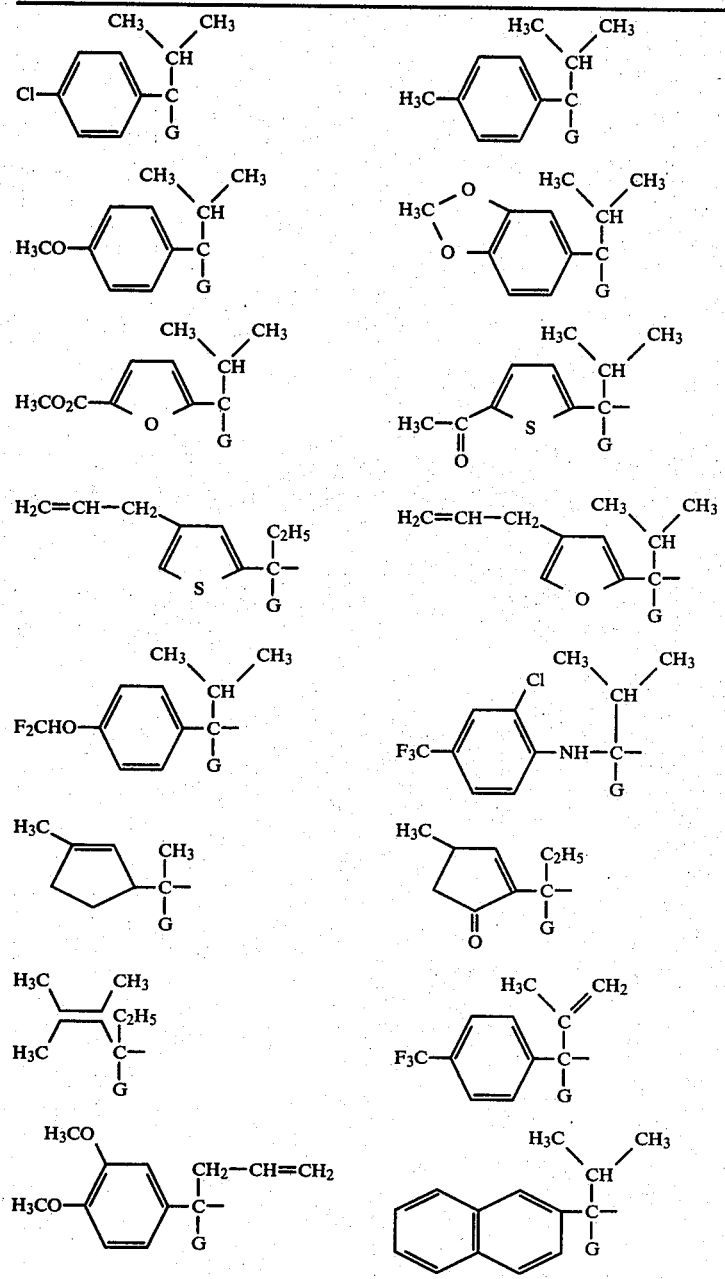

TABLE 1-continued
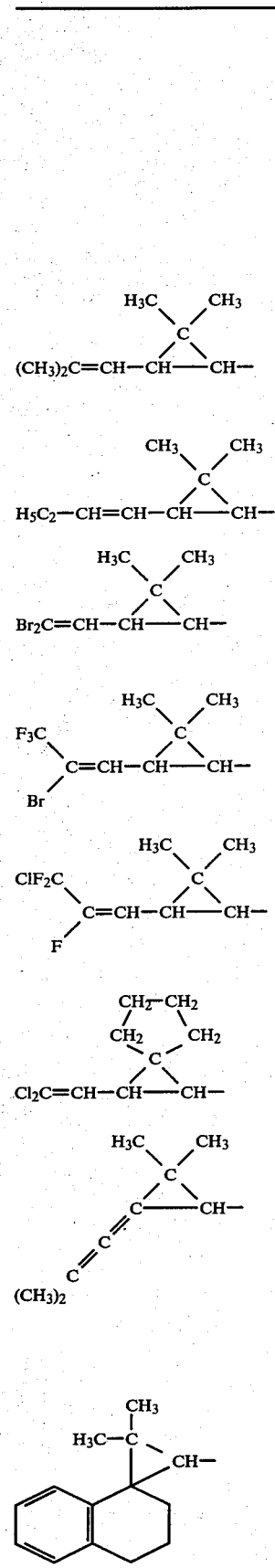
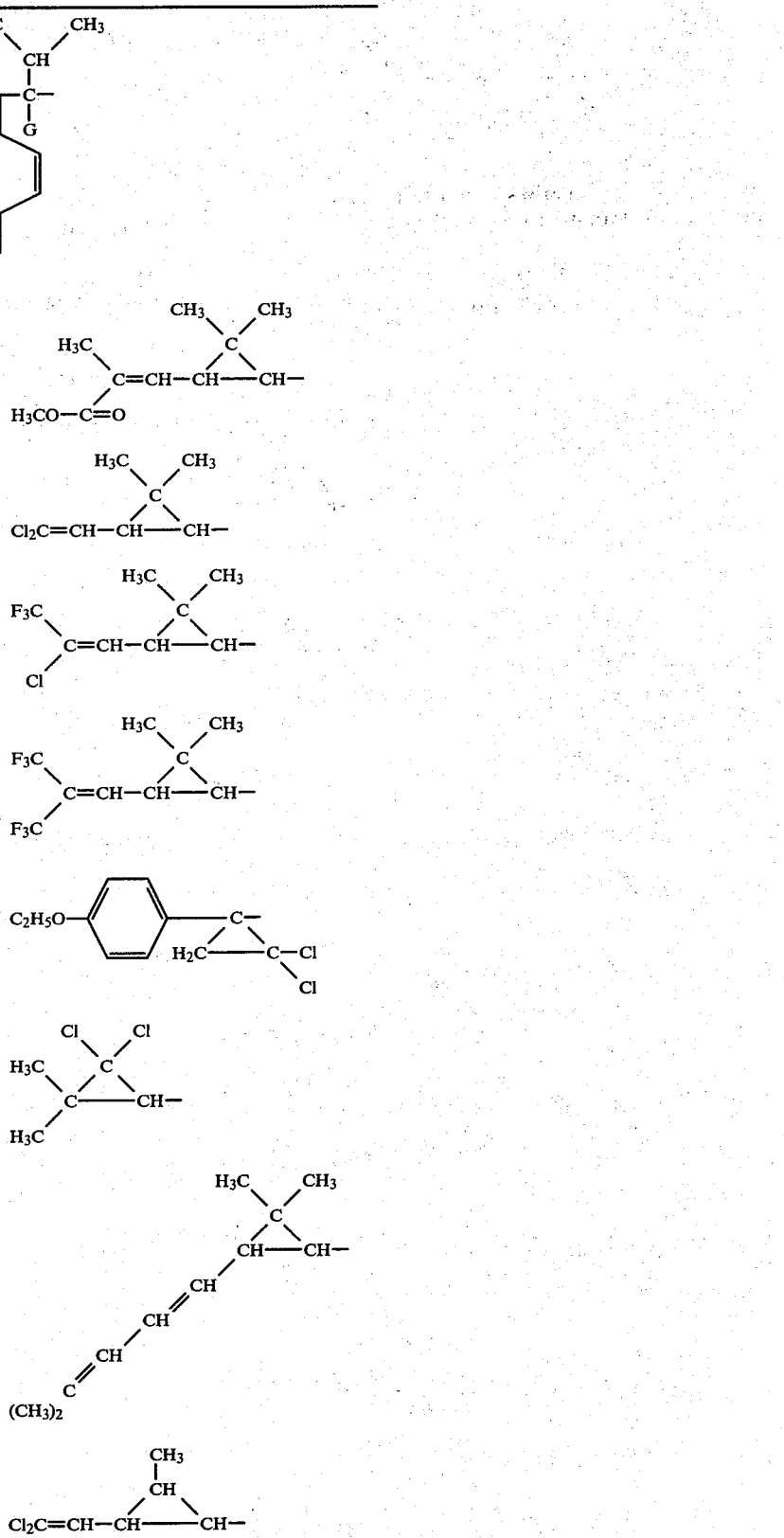

TABLE 1-continued

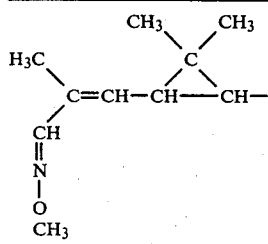 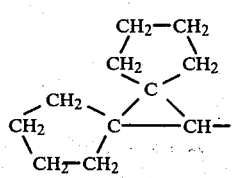

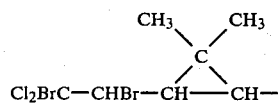

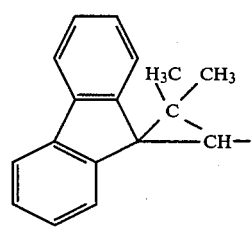 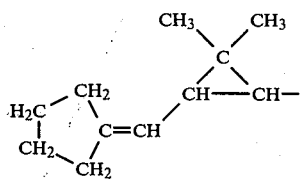

As hereinbefore indicated, the compounds of the invention of formula I have a chiral centre. Therefore, optically active or enantiomeric compounds of the invention of formula I may be prepared.

Methods for the resolution of optically active α-amino substituted acetonitriles, including arylacetonitriles, are well known in the art. U.S. Pat. No. 4,072,698 summarizes the art relevant to the resolution of optically active α-aminoacetonitriles, with particular reference to α-aminophenylacetonitrile, and discloses a process for producing an optically pure enantiomer of an α-substituted-α-aminoacetonitrile. For example, U.S. Pat. No. 4,072,698 describes the resolution of racemic α-amino-α-phenylacetonitrile using 1-(+)-tartaric acid and acetone as catalyst to give a 72% yield of D-(+)-α-amino-α-phenylacetonitrile-hydrogen-L-(+)-tartrate and the treatment of that salt with sodium carbonate to give a 69% yield optically pure D-(+)-α-amino-α-phenylacetonitrile.

Optically active or enantiomeric compounds of the invention of formula I may be prepared from racemic compounds of the invention of formula I by the same or analogous procedures to those described above. For example, a racemic compound of formula Ia may be resolved to give an optically active compound of formula Ia and the optically active compound of formula Ia may be alkylated to give an optically active compound of formula Ib. Alternatively, a racemic compound of formula Ia may be alkylated to give a racemic compound of formula Ib and the racemic compound of formula Ib resolved to give an optically active compound of formula Ib. In a further option, a racemic α-aryl(-α-aminoacetonitrile of formula III may be resolved to give an optically active compound of formula III and the optically active compound of formula III may be alkylated to give an optically active compound of the invention of formula Ia or formula Ib. Typically reaction processes are illustrated in SCHEME E below.

It is well known in the art that in pyrethroids which comprise the ester of an α-cyanophenoxybenzyl alcohol, the insecticidal activity of the (S) alcohol esters is, in general, much greater than that of the corresponding (R) alcohol esters. Thus the resolved compounds of the invention of formula I, in particular the (R)-isomers, are useful intermediates in the preparation of pyrethroids comprising a resolved alcohol moiety. For example, the (R)-isomers of the compounds of the invention of formula I may be used to give a stereospecific synthesis of pyrethroids comprising an (S) α-cyanophenoxybenzyl alcohol moiety by reaction with a pyrethrin acid or a pyrethroid acid in a nucleophilic displacement involving Walden inversion.

Therefore, pyrethroids of formula X containing a resolved α-cyanophenoxybenzyl alcohol moiety may be prepared by reacting a resolved compound of the invention of formula Ib with a carboxylic acid derivative of formula IX, or a salt thereof, according to the process hereinbefore described. A typical reaction process is illustrated in SCHEME F below.

SCHEME E
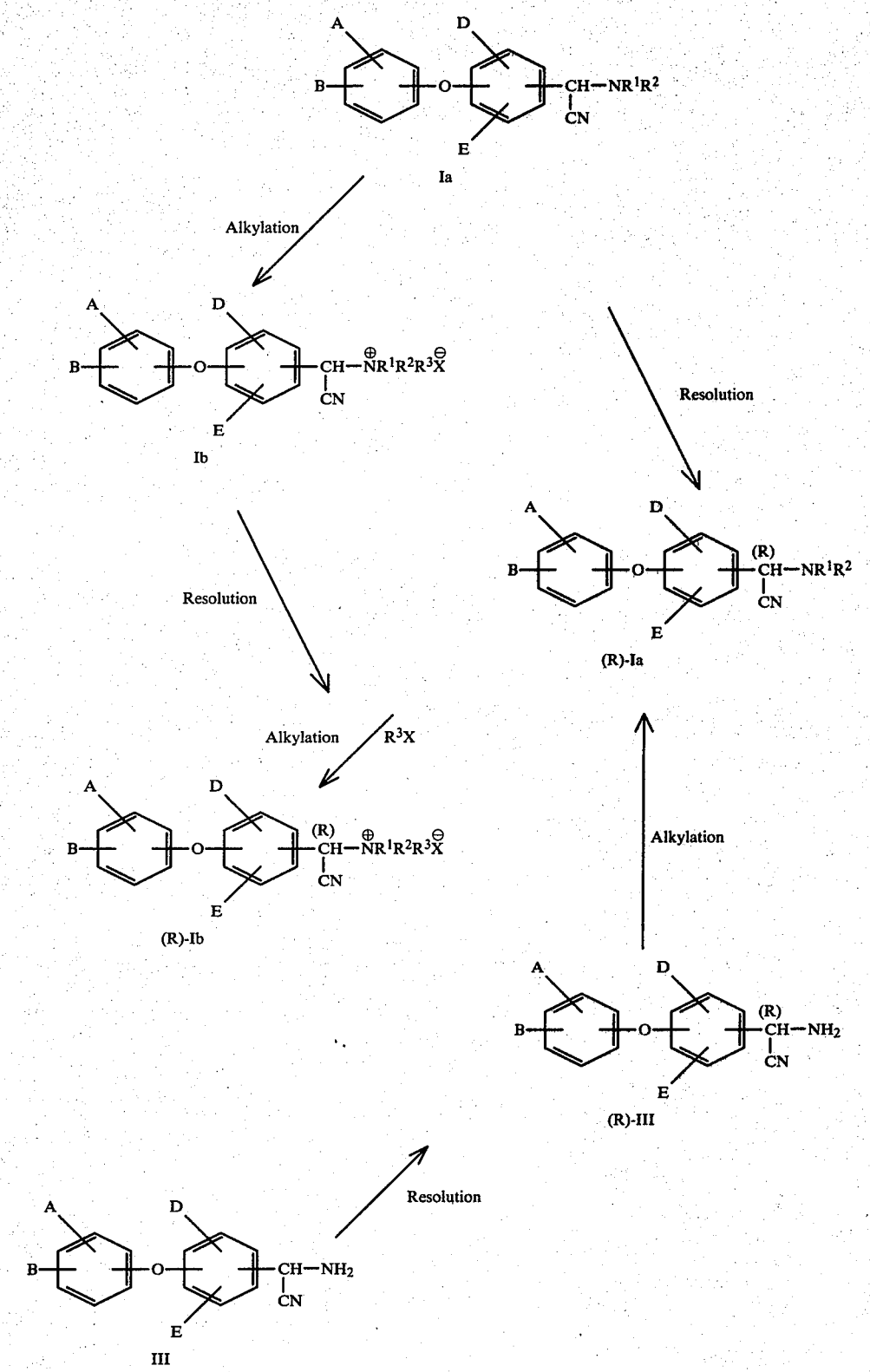

SCHEME F

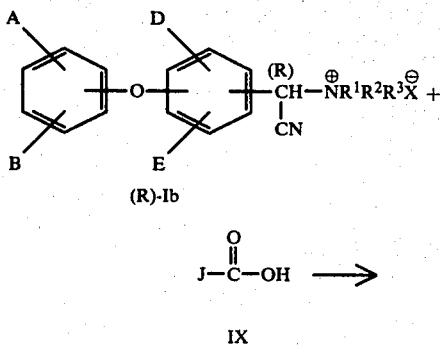

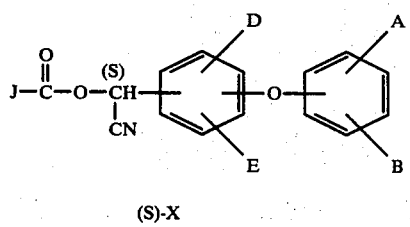

The invention is now illustrated by the following non-limiting examples.

EXAMPLE 1

α-(Dimethylamino)-3-phenoxybenzeneacetonitrile (1)

A solution of dimethylamine in water (5 ml of a 26% w/v solution; 30 mmole) and water (5 ml) was neutralised with concentrated hydrochloric acid. 3-Phenoxybenzaldehyde (3.96 g, 20 mmole) was added to the stirred solution followed by sodium cyanide (1.5 g, 30 mmole) and "Teric" N8 (5 drops of a 10% aqueous solution; "Teric" is an ICI Australia Limited Trade Mark and "Teric" N8 is the product of condensation of nonylphenol and ethylene oxide in the mole ratio of 1:8). The mixture was stirred vigorously for a period of 1 hour and then dichloromethane (50 ml) was added. The organic phase was separated, washed with water and dried over anhydrous sodium sulfate. The solvent was removed by distillation under reduced pressure to give the title compound as a pale yellow oil (5.2 g). Proton magnetic resonance spectrum (CDCl$_3$; δ in ppm): 2.3 (6H, s, N(CH$_3$)$_2$); 4.8 (1H, s, CH); 6.9–7.6 (9H, m, aromatic protons).

EXAMPLE 2

N-(α-Cyano-3-phenoxybenzyl)-N,N,N-trimethylammonium methylsulfate (4)

Dimethyl sulfate (2.52 g) was added to a solution of α-(dimethylamino)-3-phenoxybenzeneacetonitrile (5.2 g) in ethyl methyl ketone (40 ml) and the mixture was stirred overnight at ambient temperature. The solvent was removed by distillation under reduced pressure to give the title compound (7.7 g) as a golden oil. Proton magnetic resonance spectrum (CDCl$_3$; δ in ppm): 3.4 (9H, s, N(CH$_3$)$_3$); 3.65 (3H, s, CH$_3$SO$_4$); 6.7 (1H, s, CH); 7.0–7.7 (9H, m, aromatic protons).

EXAMPLE 3

α-(1-Pyrrolidinyl)-3-phenoxybenzeneacetonitrile (3)

A solution of pyrrolidine (2.13 g, 30 mmole) in water (10 ml) was neutralised with concentrated hydrochloric acid. 3-Phenoxybenzaldehyde (3.96 g; 20 mmole) was added to the stirred solution followed by sodium cyanide (1.5 g; 30 mmole) and "Teric" N8 (5 drops of a 10% aqueous solution). The mixture was stirred vigorously for a period of 1 hour and then dichloromethane (50 ml) was added. The organic phase was separated, washed with water and dried over anhydrous sodium sulfate. The solvent was removed by distillation under reduced pressure to give the title compound as a yellow oil (5.0 g). Proton magnetic resonance spectrum (CDCl$_3$; δ in ppm): 1.8 (4H, m, pyrrolidine ring β-protons); 2.6 (4H, m, pyrrolidine ring α-protons); 5.0 (1H, s, CH); 7.0–7.6 (9H, m, aromatic protons). Infra-red spectrum (liquid film; $\nu_{max}$ in cm$^{-1}$): 2950 (m) (m); 2800(m); 1580(s); 1480(s); 1240(s); 840(m); 740(m).

EXAMPLE 4

N-(α-Cyano-3-phenoxybenzyl)-N-methylpyrrolidinium methylsulfate (5) was prepared from α-(1-pyrrolidinyl)-3-phenoxybenzeneacetonitrile (Example 3) and dimethyl sulfate following essentially the same procedure as that described in Example 2. The product was obtained as a yellow oil. Proton magnetic resonance spectrum (CDCl$_3$; ε in ppm): 2.4 (4H, m, pyrrolidine ring β-protons); 3.2 (4H, m, pyrrolidine ring α-protons); 3.2–3.8 (6H, m, N—CH$_3$ and CH$_3$SO$_4$); 6.8 (1H, s, CH); 7.0–7.7 (9H, m, aromatic protons).

EXAMPLE 5

α-(Di-n-propylamino)-3-phenoxybenzeneacetonitrile (2) was prepared from 3-phenoxybenzaldehyde, di-n-propylamine and sodium cyanide following essentially the same procedure as that described in Example 1. The product was isolated as a golden oil.

EXAMPLE 6

(R,S)-α-Cyano-3-phenoxybenzyl (±)-cis-3-(Z-2-chloro-3,3,3-trifluoroprop-1-enyl)-2,2-dimethylcyclopropanecarboxylate A mixture of N-(α-cyano-3-phenoxybenzyl)-N,N,N-trimethylammonium methylsulfate (3.7 g; see Example 2), sodium (±)-cis-3-(Z-2-chloro-3,3,3-trifluoroprop-1-enyl)-2,2-dimethylcyclopropanecarboxylate (2.42 g) and methyl isobutyl ketone (5 ml) was heated under reflux for a period of 1 hour after which time the mixture had thickened to a gel. The mixture was diluted with water (100 ml) and dichloromethane (100 ml). The organic phase was separated, dried over anhydrous sodium sulfate, and the solvent was removed by distillation under reduced pressure to give the product. The product was identified as the title compound by comparison with an authentic sample of the title compound. The product and authentic sample showed identical properties on thin layer chromatography (silica gel; eluent toluene) and vapour phase chromatography (2 foot column, 5% 80–100 Carbowax 20 M on OV 17). The proton magnetic resonance spectra of the product and the authentic sample were identical.

EXAMPLES 7 TO 15

(R,S)-α-Cyano-3-phenoxybenzyl (±)-cis-3-(Z-2-chloro-3,3,3-trifluoroprop-1-enyl)-2,2-dimethylcyclopropanecarboxylate A mixture of N-(α-cyano-3-phenoxybenzyl)-N,N,N-trimethylammonium methylsulfate (0.01 mole), the sodium or potassium salt of (±)-cis-3-(Z-2-chloro-3,3,3- trifluoroprop-1-enyl)-2,2-dimethylcyclopropanecarboxylate (0.01 mole) and a solvent were stirred together.

The carboxylate salt cation, the solvent and the reaction conditions are detailed in Table 2. The yield of the product, (R,S)-α-cyano-3-phenoxybenzyl (±-cis-3-(Z-2-chloro-3,3,3-trifluoroprop-1-enyl)-2,2-dimethylcyclopropanecarboxylate, was for each Example determined by vapor phase chromatography (column—45 cm 10% OVIOI; temperature 140° C. for 2 min, 40°–270° C. at 32°/min, 270° C. for 2 min) using diethyl phthalate as internal standard and a digital integrator (Hewlett Packard 3390A). The yields are recorded in Table 2.

In Example 14 the yield of product as determined by gas-liquid chromatography was confirmed by isolation of the product using column chromatography over silica gel.

TABLE 2

| Example | Cation | Solvent | Solvent Volume (ml) | Reaction Temp (°C.) | Reaction Time (hr) | Product Yield (g) |
|---|---|---|---|---|---|---|
| 7 | K$^\oplus$ | MEK | 5 | 20 | 72 | 2.6 |
| 8 | K$^\oplus$ | MEK | 5 | 40 | 48 | 2.1 |
| 9 | K$^\oplus$ | MEK | 20 | Reflux | 5 | 2.2 |
| 10 | K$^\oplus$ | NM | 5 | 40 | 24 | 2.3 |
| 11 | K$^\oplus$ | NM | 5 | 40 | 48 | 2.4 |
| 12 | K$^\oplus$ | A | 5 | 20 | 24 | 2.3 |
| 13 | K$^\oplus$ | MIBK | 20 | Reflux | 3 | 2.3 |
| 14 | K$^\oplus$ | MIBK | 15 | Reflux | 2 | 2.2 |
| 15 | Na$^\oplus$ | MIBK | 15 | Reflux | 2 | 1.8 |

Solvent Code:
MEK — methyl ethyl ketone
NM — nitromethane
A — acetone
MIBK — methyl isobutyl ketone

EXAMPLE 16

α-(N-Isobutyl-N-methylamino)-3-phenoxybenzeneacetonitrile (10)

(a) 3-Phenoxybenzaldehyde, isobutylamine hydrochloride and sodium cyanide were reacted on a 0.3 molar scale using essentially the same procedure as that described in Example 1. The product, α-(N-isobutylamino)-3-(phenoxybenzeneacetonitrile, was obtained as a golden oil (43.5 g). Proton nuclear magnetic resonance spectrum (d$_6$-acetone; δ in ppm): 0.9 (6H, d of d); 1.74 (1H, m); 2.52 (2H, d); 5.02 (1H, s); 6.9–7.6 (9H, m).

(b) A mixture of α-(N-isobutylamino)-3-phenoxybenzeneacetonitrile (28.0 g; 0.1 mole), dimethyl sulfate (12.6 g; 0.1 mole), anhydrous potassium carbonate (15.0 g) and anhydrous acetone (100 ml) was stirred at a temperature of 50° C. for a period of 16 hours. The mixture was filtered and the solvent was removed from the filtrate by distillation under reduced pressure. The residue was treated with anhydrous diethyl ether, the etherial solution was separated and the ether was evaporated to give α-(N-isobutyl-N-methylamino)-3-phenoxybenzeneacetonitrile as a yellow oil. Proton nuclear magnetic resonance spectrum (d$_6$-acetone; δ in ppm): 0.85 (6H, d of d); 1.83 (1H, m); 2.23 (3H, s); 5.19 (1H, s); 7.0–7.5 (9H, m).

EXAMPLE 17

N-(α-Cyano-3-phenoxybenzyl)-N-isobutyl-N,N-dimethylammonium methyl sulfate (11)

A mixture of α-(N-isobutyl-N-methylamino)-3-phenoxybenzeneacetonitrile (7.35 g) and dimethyl sulfate (3.15 g) was stirred at a temperature of 100° C. for a period of 4 hours to give N-(α-cyano-3-phenoxybenzyl)-N-isobutyl-N,N-dimethylammonium methyl sulfate. Proton nuclear magnetic resonance spectrum (d$_6$-acetone; δ in ppm): 1.18 (6H, d of d); 3.45 (3H, s); 3.53 (3H, s); 6.84 (1H, s); 7.0–7.7 (9H, m).

EXAMPLE 18

(R,S)-α-Cyano-3-phenoxybenzyl (±)-cis-3-(Z-2-chloro-3,3,3-trifluoroprop-1-enyl)-2,2-dimethylcyclopropanecarboxylate A mixture of N-(α-cyano-3-phenoxybenzyl)-N-isobutyl-N,N-dimethylammonium methylsulfate (3.08 g), potassium (±-(cis-3-(Z-2-chloro-3,3,3-trifluoroprop-1-enyl)-2,2-dimethylcyclopropanecarboxylate (2.42 g) and methyl ethyl ketone was stirred at a temperature of 40° C. for a period of 24 hours. The reaction mixture was worked up as described in Example 6 to give the title compound as a golden oil (1.66 g). The product had identical properties to the product prepared in Example 6 and to authentic material prepared by a different route.

EXAMPLE 19

(R,S)-α-Cyano-3-phenoxybenzyl (±) cis/trans-3-(2,2-dichlorovinyl)-2,2-dimethylcyclopropanecarboxylate (cis/trans ratio 45:55)

A mixture of potassium (±)-cis/trans-3-(dichlorovinyl)-2,2-dimethylcyclopropanecarboxylate (cis/trans ratio 45:55) and N-(α-cyano-3-phenoxybenzyl)-N,N,N-trimethylammonium methylsulfate were reacted following essentially the same procedure as that described in Example 7. The reaction mixture was worked up as described in Example 6 to give the title compound as an oil.

The product was identified by comparison with an authentic sample of the title compound. The product and authentic sample showed identical properties on thin layer chromatography (silica gel; eluent toluene) and vapour phase chromatography (45 cm column, 10% OVIOI).

We claim:

1. A compound of formula I

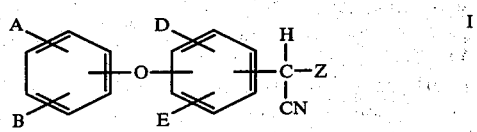

wherein:
A, B, D and E are independently chosen from the group consisting of hydrogen, halogen, C$_1$ to C$_6$ alkyl, C$_1$ to C$_6$ haloalkyl and C$_1$ to C$_6$ alkoxy; and Z is chosen from NR$^1$R$^2$ and N$^\oplus$R$^1$R$^2$R$^3$X$^\ominus$
wherein:
R$^1$ and R$^2$ are idependently chosen from the group consisting of C$_1$ to C$_6$ alkyl, phenyl, benzyl, and the groups phenyl and benzyl wherein in each group the phenyl ring is substituted with from one to three substituents chosen from the group consisting of halogen, nitro, cyano, hydroxy, C$_1$ to C$_6$ alkyl, C$_1$ to C$_6$ alkoxy and C$_1$ to C$_6$ haloalkyl, or R$^1$ and R$^2$ are linked to form a heterocyclic ring chosen from the group consisting of 1-pyrrolyl, 1-imidazolyl, 1-pyrrolidinyl, 1-pyrrolinyl, 1-imidazolinyl, piperidino, 1-piperazinyl and morpholino;

$R^3$ is chosen from the group consisting of $C_1$ to $C_6$ alkyl, phenyl, benzyl, and the groups phenyl and benzyl wherein in each group the phenyl ring is substituted with from one to three substituents chosen from the group consisting of halogen, nitro, cyano, hydroxy, $C_1$ to $C_6$ alkyl, $C_1$ to $C_6$ alkoxy and $C_1$ to $C_6$ haloalkyl, or $N^\oplus R^1R^2R^3$ is a pyridinium, pyrazinium, pyrimidinium or pyridazinium ring; and $X^\ominus$ is the anion of an organic or an inorganic acid.

2. A compound according to claim 1 wherein: A, B, D and E are independently chosen from the group consisting of hydrogen, halogen, methyl, trifluoromethyl and methoxy; and Z is chosen from the groups $NR^1R^2$ and $N^\oplus R^1R^2R^3X^\ominus$ wherein:

$R^1$ and $R^2$ are independently chosen from the group consisting of $C_1$ to $C_4$ alkyl, phenyl and benzyl or $R^1$ and $R^2$ are linked together to form a heterocyclic ring chosen from the group consisting of 1-pyrrolyl, 1-imidazolyl, 1-pyrrolidinyl, 1-pyrrolinyl, 1-imidazolinyl, piperidino, 1-piperazinyl and morpholino;

$R^3$ is chosen from the group consisting of $C_1$ to $C_4$ alkyl, phenyl and benzyl or $N^\oplus R^1R^2R^3$ is a pyridinium, pyrazinium, pyrimidinium or pyridazinium ring; and $X^\ominus$ is the anion of a strong acid.

3. A compound according to claim 2 wherein:
A, B, D and E are independently chosen from hydrogen and halogen; and Z is chosen from the groups $NR^1R^2$ and $N^\oplus R^1R^2R^3X^\ominus$ wherein:

$R^1$ and $R^2$ are independently chosen from $C_1$ to $C_4$ alkyl or $R^1$ and $R^2$ are linked to form a heterocyclic ring chosen from the group consisting of 1-pyrrolyl, 1-pyrrolidinyl, piperidino and morpholino;

$R^3$ is chosen from $C_1$ to $C_4$ alkyl; and $X^\ominus$ is the anion of a strong acid.

4. A compound according to claim 1 wherein in the compound of formula I the phenyl ring of the benzyl group is substituted in the 3-position by the phenoxy group to give a compound of formula II

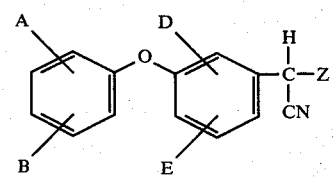

5. A compound according to claim 4 wherein:
A, B, D and E are hydrogen; and
Z is chosen from the group consisting of N,N-dimethylmino, 1-pyrrolidinyl, N,N-di(n-propyl)amino, N-isobutyl-N-methylamino, N,N,N-trimethylammonio methyl sulfate, and N-isobutyl-N,N-dimethylammonio methyl sulfate.

6. A compound according to claim 1 wherein Z is the group $-N^\oplus R^1R^2R^3X^\ominus$.

* * * * *